United States Patent [19] [11] 4,166,178
Tsushima et al. [45] Aug. 28, 1979

[54] 3-ACYLOXYMETHYL-CEPHEM COMPOUNDS

[75] Inventors: Susumu Tsushima, Suita; Michiyuki Sendai, Osaka; Mitsuru Shiraishi, Suita; Norichika Matsumoto, Neyagawa, all of Japan

[73] Assignee: Takeda Chemical Industries, Ltd., Osaka, Japan

[21] Appl. No.: 897,157

[22] Filed: Apr. 17, 1978

Related U.S. Application Data

[63] Continuation of Ser. No. 683,800, May 6, 1976, abandoned.

[30] Foreign Application Priority Data

May 6, 1975 [JP] Japan ................................. 50-55020
Jan. 1, 1976 [JP] Japan ................................. 51-1275

[51] Int. Cl.² .................. C07D 501/20; A61K 31/545
[52] U.S. Cl. ........................................ 544/16; 544/22; 544/30; 424/246
[58] Field of Search .................... 544/16, 22, 30

[56] References Cited

U.S. PATENT DOCUMENTS 3,941,774  3/1976  Clayton et al. ................. 544/16

Primary Examiner—Nicholas S. Rizzo
Assistant Examiner—James H. Turnipseed
Attorney, Agent, or Firm—Wenderoth, Lind & Ponack

[57] ABSTRACT

Novel 3-acyloxymethyl-cephem compounds of the formula:

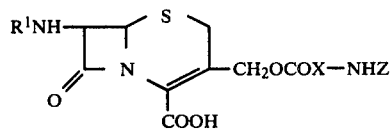

wherein $R^1$ is hydrogen or an acyl group; X is a divalent group consisting of a carbon chain having 2 to 3 carbon atoms and a carbonyl or sulfonyl group at one terminal end thereof, said divalent group being either substituted or unsubstituted on the carbon chain; and Z is an organic acid residue, and salts thereof were found to be useful as starting materials for preparing cephalosporins of the formula:

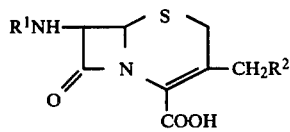

wherein $R^2$ stands for a residue of a nucleophilic compound and $R^1$ has the same meaning as above.

25 Claims, No Drawings

3-ACYLOXYMETHYL-CEPHEM COMPOUNDS

This is a continuation of application Ser. No. 683,800, filed May 6, 1976 now abandoned.

The present invention relates to novel 3-acyloxymethyl-cephem compounds and preparations thereof. More particularly, this invention relates to the compounds of the formula (I);

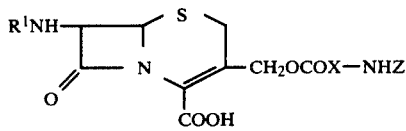

wherein $R^1$ is hydrogen or an acyl group; X is a divalent group consisting of a carbon chain having 2 to 3 carbon atoms and a carbonyl or sulfonyl group at one terminal end thereof, said divalent group being either substituted or unsubstituted on the carbon chain; and Z is an organic acid residue, and pharmaceutically acceptable salts thereof, and also relates to processes for producing them.

Cephalosporin derivatives with a 3-hydroxymethyl moiety were only obtainable by enzymatic cleavage of the 3-acetyl group from 3-acetoxymethyl-cephalosporins or by separating them from the cephalosporin C fermentation by-product. Recently, it has become possible to produce 7β-(D-5-amino-5-carboxyvaleramido)-3-hydroxymethyl-3-cephem-4-carboxylic acid (deacetyl-cephalosporin C, DCPC) in high titer by fermentation (U.S. Pat. No. 3,926,726, Nature New Biology, 246, 154(1973)) and, alongside of cephalosporin C, this substance has been attracting attention as a starting material for cephalosporin compounds that could be more potent in antibiotic activity.

It has, however, been believed to be difficult to acylate the 3-hydroxymethyl group of the 3-hydroxymethyl compound (cephalosporadesic acid). For example, Heyningen [Van Heyningen: J. Med. Chem., 8, 22(1965), Advan. Drug. Res., 4, 28(1968)] reported that the O-acylation of cephalosporadesic acid was feasible only with the use of a large excess of aroyl chloride (yield 32%-57%) and that the use of ketene, aliphatic acid chloride or acetic anhydride did not cause the O-acylation, or induced a lactonization. Kukolja [J. Med. Chem., 13, 1114(1970)] reported a roundabout process for the synthesis of O-acyloxymethylcephalosporins which comprised O-acylating a 3-hydroxymethyl-2-cephem compound and then causing the latter to become isomerized to the 3-cephem compound. U.S. Pat. No. 3,532,694 and Japanese Patent Publication No. 33080/1975 disclosed a process in which, to prevent the lactonization reaction, the 4-carboxyl group of cephalosporadesic acid is first protected, for example by esterification and, then, the O-acylation is carried out. Disclosed in Japanese Patent Application as Laid Open No. 42792/1972 is a process which comprises O-acylating cephalosporadesic acid with azolide. However, these processes are not commercially profitable because they provide only low yields or/and involve troublesome and time-comsuming procedures or/and expensive reagents, for instance. Thus, for example, the esterification reaction of cephalosporadesic acid cannot be accomplished by an ordinary esterification process in which the rearrangement of the double bond or the lactonization predominates. While it is possible to introduce such limited groups as, e.g., methyl, ethyl, diphenylmethyl or benzyl by means of diazo compounds which as diazomethane, diazoethane, diphenyldiazomethane, phenyldiazomethane, for example, it is difficult, after 3-acylation, to de-esterify the compound without the accompaniment of some side reaction such as a fission of the β-lactam ring or a shift of the double bond.

On the other hand, the reaction by which the 3-acetoxymethyl group of a cephalosporin compound is substituted with a nucleophilic reagent entails a concurrent decomposition of the starting material, intermediate and product in its course and a protracted reaction time, and therefore results in lower yields [A. B. Tayor, J. Chem. Soc., 7020(1965)]. Thus, it has been desired to have available a derivative possessing a group which will lend itself more readily to substitution than the acetoxy group.

To overcome the foregoing problems we undertook extensive research, which led us to the finding that the use of compounds [IV] hereinafter described as an acylating agent would enable cephalosporadesic acid to be O-acylated in a high yield, and that the O-acylated cephalosporin thus synthesized would undergo the desired substitution with a nucleophilic compound with great ease. This invention has been developed on the basis of the above findings.

The above compounds [I] include the compounds wherein $R^1$ is hydrogen, phenylacetyl, phenoxyacetyl, 5-amino-5-carboxyvaleryl whose amino or/and carboxyl groups may optionally be protected, or any of the groups found in the 6- or 7-positions of penicillin or cephalosporin derivatives, as the case may be. Thus, for example, the acyl group $R^1$ may be chosen from among aliphatic acyl groups such as formyl, acetyl, propionyl, butyryl, isobutyryl, valeryl, isovaleryl, cyclopentylcarbonyl, cyclohexylcarbonyl, cycloheptylcarbonyl, cyclopentylacetyl, cyclohexadienylacetyl, etc.; aromatic acyl groups such as benzoyl, p-nitrobenzoyl, toluoyl, naphthoyl, etc.; mono-substituted aliphatic acyl groups such as 2-thienylacetyl, cyanoacetyl, acetoacetyl, 4-chloro-3-oxobutyryl, 4-bromo-3-oxobutyryl, chloroacetyl, bromoacetyl, 4-methylthio-3-oxobutyryl, 4-carbamoylmethylthio-3-oxobutyryl, α-phenoxypropionyl, α-phenoxybutyryl, tetrazolylthioacetyl, tetrazolylacetyl, p-nitrophenylacetyl, trifluoromethylthioacetyl, trifluoromethylsulfinylacetyl, trifluoromethylsulfonylacetyl, cyanomethylthioacetyl, thiadiazolylthioacetyl, p-nitrophenylacetyl, (2-pyridyloxy)acetyl, (2-oxo-4-thiazolin-4-yl)acetyl, (2-imino-4-thiazolin-4-yl)acetyl, (2-thioxo-4-thiazolin-4-yl)acetyl, 4-pyridylthioacetyl, (3-sydnone)acetyl, 1-pyrazolylacetyl, 2-furylacetyl, (2-oxo-3-methylpyridazinyl)thioacetyl, (2-aminomethylphenyl)acetyl, (2-aminomethylcyclohexenyl)acetyl, etc.; di-substituted aliphatic acyl groups such as α-carboxyphenylacetyl, mandelyl, α-sulfophenylacetyl, α-sulfo-(p-aminophenyl)acetyl, phenylglycyl, (4-hydroxyphenyl)glycyl, (4-methylthiophenyl)glycyl, (4-methoxyphenyl)glycyl, (4-methanesulfinylphenyl)glycyl, (3-methanesulfonamidophenyl)glycyl, 1-cyclohexenylglycyl, thienylglycyl, furylglycyl, cyclohexadienylglycyl, (3,4-dihydroxyphenyl)glycyl, etc.; 5-methyl-3-phenyl-4-isoxazolylcarbonyl; 3-(2,6-dichlorophenyl)-5-methyl-4-isoxazolylcarbonyl; and so forth. It should be understood that the above-mentioned groups are only illustrative of the acyl groups that are capable of use for the purposes of this invention, but preferred acyl groups may be represented by the formula (A):

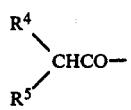

(A)

wherein R⁴ represents a group such as, for example, acetyl, halogenoacetyl, phenyl, p-hydroxyphenyl, thienyl, 2-imino-4-thiazolin-4-yl, 2-oxo-4-thiazolin-4-yl, tetrazolyl, phenoxy, 3-amino-3-carboxypropyl, and R⁵ represents a substituent such as, for example, hydrogen, sulfo, amino or hydroxy, etc.

It should also be understood that any functional groups, e.g. amino or/and carboxyl, in such acyl groups may be suitably protected by conventional protective groups. Thus, among such protective groups for the amino groups are aromatic acyl groups such as phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, etc.; aliphatic acyl groups such as acetyl, valeryl, capryl, n-decanoyl, acryloyl, pivaloyl, camphorsulfonyl, methanesulfonyl, chloroacetyl, etc.; esterified carboxyl groups such as tert-butoxycarbonyl, ethoxycarbonyl, isobornyloxycarbonyl, phenyloxycarbonyl, trichloroethoxycarbonyl, benzyloxycarbonyl, β-methylsulfonylethoxycarbonyl, etc.; carbamoyl groups such as methylcarbamoyl, phenylcarbamoyl, naphthylcarbamoyl, etc.; the corresponding thiocarbamoyl groups; 2-methoxycarbonyl-1-methylvinyl; and so forth. As protective groups for the carboxyl groups of such acyls R¹ and the 4-carboxyl group of the cephem ring, there may be mentioned methyl, ethyl, tert-butyl, tert-amyl, benzyl, p-nitrobenzyl, p-methoxybenzyl, benzhydryl, 1-indanyl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, silyl groups such as trimethylsilyl, dimetlylsilyl, etc.; and so forth. These carboxyl groups, however, may be preferably in the form of inorganic or organic salts with alkali metals such as lithium, sodium, potassium, etc.; alkaline earth metals such as calcium, magnesium, or various amines such as dicyclohexylamine, triethylamine, tributylamine, di-n-butylamine, di-n-propylamine and so forth.

The divalent group X means a hydrocarbon group which has a carbonyl or sulfonyl group at one of its terminal ends and which is normally able to form a five-membered or six-membered ring with

and may be interrupted by, or include at one terminal end thereof, an unsaturation such as a double bond or oxygen or/and sulfur atoms. The hydrocarbon chain may further carry suitable substituents. As examples of such substituents on said hydrocarbon chain, there may be mentioned alkyl groups such as methyl, ethyl, propyl, etc.; aralkyl groups such as benzyl, phenethyl, etc.; and aryl groups such as phenyl, tolyl, etc. Where two or more such substituents are present, they may form a cyclic structure with the hydrocarbon chain. The symbol Z is a group exemplified by lower alkoxycarbonyl groups such as methoxycarbonyl, ethoxycarbonyl, etc.; acyl groups such as acetyl, propionyl, benzoyl, chloroacetyl, etc.; other organic acid residues, e.g. sulfonyl derivatives such as phenylsulfonyl, tosyl, mesyl, etc.; and carbamoyl groups; phosphorous derivatives such as diethylphosphoro, dimethylphosphono, diethylphosphino, dimethylphosphino, and so forth.

Those compounds [I] can be produced by reacting a compound of the formula:

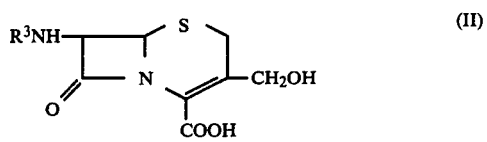

(II)

wherein R³ is hydrogen or an acyl group, with a compound of the general formula:

(IV)

wherein the various symbols are as defined above.

Thus, compound [IV] is exemplified by N-carboethoxyphthalimide, N-carbomethoxypathalimide, 4-nitro-N-carboethoxyphthalimide, 3-nitro-N-carboethoxyphthalimide, N-carboethoxysuccinimide, N-carbomethoxysuccinimide, N-tosylphthalimide, N-methylsulfonylphthalimide, N-benzenesulfonylphthalimide, N-acetylphthalimide, N-chloroacetylphthalimide, N-acetylsuccinimide, N-carboethoxysaccharin, N-acetylsaccharin, N-benzoylsaccharin, N-carboethoxymaleimide, N-carboethoxyglutarimide, N-carboethoxy-(p-chlorophenyl)succinimide, N-carboethoxyisatin, N-carbomethoxyisatin, N-acetylisatin, N-(methylcarbamoyl)isatin, N-(phenylcarbamoyl)isatin, N-(β-methylsulfonylethoxycarbonyl)isatin, N-(diethylphosphoro)succinimide, N-(dimethylphosphoro)succinimide, N-(dimethylphosphino)succinimide, N-(diethylphosphino)phthalimide and so forth.

Generally the reaction of compound [II] with compound [IV] is conveniently carried out in the presence of an appropriate inert solvent. Among the common solvents used in this reaction are dichloromethane, chloroform, dichloroethane, ethyl acetate, acetonitrile, acetone, tetrahydrofuran, dimethylformamide, dimethylacetamide, dioxane, ether and mixtures of such solvents. This reaction is a stoichiometrically equivalent reaction, that is to say, [II] and [IV] may be reacted in equimolar proportions, although an excess of [IV] may be used to hasten the reaction, to compensate for the decomposition of [IV] or for other considerations. Generally the reaction may be conducted at room temperature or under cooling (for example, −10° C. to −40° C.), preferably at 0° to 30° C. The reaction normally goes to completion within a short time, but in view of the nature of the reaction, which is somewhat temperature-dependent, the reaction is usually carried out for 0.5 to 15 hours so as to ensure a thorough completion of the reaction. If necessary, an amine exemplified by triethylamine may be added to the reaction system. Where the starting compounds [II] is an alkali metal salt, a salt interchange may be effected by the addition of an equivalent of triethylamine hydrochloride or the like before the said reaction is conducted.

Where starting compounds [II] contain a free, unprotected amino group, this amino group is acylated simulteneously with the acylation of the 3-hydroxyl group by the same acyl group under the conditions of this reaction. In other words, the protective group for amino in the acyl group includes the acyl groups formed on reaction with [IV] in addition to the groups mentioned hereinbefore. The N-acylated compound [I] or [II] wherein $R^1$ or $R^3$ is an acyl group respectively, when necessary, may be converted to the corresponding compound wherein $R^1$ is hydrogen by cleaving the N-acyl group off in a manner conventional per se. The meaning of $R^3$ only differs from that of $R^1$ in these cases.

The resultant compound [I] not only has antibiotic activity as such but is ready to react with a nucleophilic compound to have the residue of said nucleophilic compound introduced into the 3-methyl group of the cephalosporin to give the compound represented by the formula [III]:

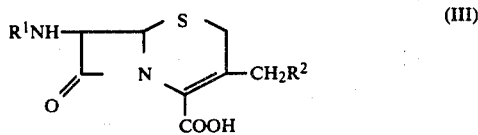

wherein $R^2$ stands for a residue of a nucleophilic compound and $R^1$ has the same meaning as defined before.

As to the nucleophilic compound used for this reaction, any compound able to replace the 3-acetoxy groups of cephalosporins may be used. Furthermore, this reaction proceeds far faster than the reaction of the 3-acetoxy compound, with an additional advantage that a substituent group which does react with the 3-acetoxy compound, which is less active, only in poor yields can be successfully introduced.

Therefore, among such nucleophilic compounds are nitrogen-containing heterocyclic thiols which contain one or more nitrogen atoms which may optionally be in the form of oxide or/and which contain such atoms as oxygen or/and sulfur in addition to the nitrogen atom, with or without nuclear substitution. As common examples of the nitrogen-containing heterocyclic group of such a thiol compound, there may be mentioned pyridyl, N-oxidepyridyl, pyrimidyl, pyridazinyl, N-oxidepyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl and so on. As the substituents on such nitrogen-containing heterocyclic groups, there may be mentioned such monovalent groups as hydroxy, mercapto, amino, carboxyl, carbamoyl, lower alkyl (for example, methyl, ethyl, trifluoromethyl, propyl, isopropyl, butyl or isobutyl), lower alkoxy (for example, methoxy, ethoxy, propoxy, isopropoxy or butoxy), halogens (e.g. chlorine or bromine), and various substituent groups attached through lower alkylene groups, —S—, —N— or other polyvalent groups. When such polyvalent groups are lower alkylene groups, the substituents may be, for example, be hydroxy, mercapto, amino, morpholino, carboxyl, sulfo, carbamoyl, alkoxycarbonyl, lower alkylcarbamoyl, alkoxy, alkylthio, alkylsulfonyl, acyloxy, morpholinocarbonyl and so on. When such a polyvalent group is —S— or —N—, the substituents may be lower alkyls or lower alkylene groups having the aforementioned substituents. When the polyvalent group is —N—, such substituents as carboxyl, alkoxycarbonyl, acyl, carbamoyl or lower alkylcarbamoyl may be directly attached. More particularly, there may be mentioned, for example, substituted alkyl groups such as carboxymethyl, carbamoylmethyl, N-lower alkylcarbamoylmethyl (e.g. N,N-dimethylcarbamoylmethyl), hydroxy lower alkyl (e.g. hydroxymethyl or 2-hydroxyethyl), acyloxy lower alkyl (e.g. acetoxymethyl or 2-acetoxyethyl), alkoxycarbonylmethyl (e.g. methoxycarbonylmethyl, hexyloxycarbonylmethyl or octyloxycarbonylmethyl), methylthiomethyl, methylsulfonylmethyl, N-lower alkylamino lower alkyl (e.g. N,N-dimethylaminomethyl, N,N-dimethylaminoethyl or N,N,N-trimethylammoniumethyl), morpholinomethyl; substituted amino groups such as lower alkylamino (e.g. methylamino), sulfo-lower alkylamino (e.g. 2-sulfoethylamino), hydroxylower alkylamino (e.g. hydroxyethylamino), lower alkylamino-lower alkylamino (e.g. 2-dimethylaminoethylamino or 2-trimethylammoniumethylamino), acylamino (e.g. acetylamino), 2-dimethylaminoacetylamino, 2-trimethylammoniumacetylamino or lower alkoxycarbonylamino (e.g. methoxycarbonylamino), etc.; and substituted thio (mercapto) groups such as methylthio, 2-hydroxyethylthio, 2-acyloxyethylthio (e.g. 2-acetoxyethylthio, 2-phenylacetoxyethylthio or 2-caproyloxyethylthio), carboxymethylthio, alkoxycarbonylmethylthio (e.g. methoxycarbonylthio or hexyloxycarbonylmethylthio), carbamoylmethylthio, N-lower alkylcarbamoylmethylthio (e.g. N,N-dimethylcarbamoylmethylthio), acetylmethylthio, N-lower alkylamino-lower alkylthio (e.g. 2-N,N-dimethylaminoethylthio or 2-N,N,N-trimethylammoniumethylthio), morpholinocarbonylmethylthio, 2-sulfoethylthio and so on. More particularly, there may be mentioned various heterocyclic thiols such as tetrazolethiol, methyltetrazolethiol, phenyltetrazolethiol, (2-N,N-dimethylaminoethyl)tetrazolethiol, methylthiadiazolethiol, hydroxyethylthiothiadiazolethiol, methylthiothiadiazolethiol, thiadiazolethiol, carbamoylaminothiadiazolethiol, carbamoylmethylthiothiadiazolethiol, thiazolethiol, methylthiazolethiol, carboxymethylthiazolethiol, triazolethiol, dimethyltriazolethiol, pyrazolethiol, ethoxycarbonylmethyltriazolethiol, imidazolethiol, methyloxadiazolethiol, pyridinethiol, pyrimidinethiol, methylpyridazinethiol, triazinethiol and so on. In addition, use may also be made of such nitrogen-containing heterocyclic compounds as aliphatic or aromatic thiols, e.g. methanethiol, ethanethiol or thiophenol; thiourea and its derivatives such as N-methylthiourea or N-methyl-N'-pyridylthiourea; thioamide derivatives such as thiosemicarbazide, thioacetamide or thiobenzamide; sodium thiosulfate, sodium sulfite, potassium thiocyanate or sodium azide; pyridine and pyridine derivatives such as quinoline, picoline, nicotinic acid, nicotinamide, isonicotinamide, isonicotinic acid hydrazide, m-bromopyridine, pyridinesulfonic acid, pyridine-m-carbinol (3-hydroxymethylpyridine), pyridinaldehyde, quinoline or isoquinoline, etc.; and such other nitrogen-containing heterocyclic compounds as pyrazine, pyrazinamide (2-carbamoylpyrazine), pyridazine, pyrimidine, imidazole, 1-methylimidazole, pyrazol and so forth. It is also possible to employ carbon nucleophilic agents toward which the 3-position is known to be refractory. As examples of such carbon nucleophilic reagents, there may be mentioned cyanides, pyrrole, substituted pyrrole, indole, acetylene, active methylene compounds, e.g. acetylacetone, acetoacetic acid esters, malonic acid esters, cyclohexane-1,3-dione, triacetylmethane or enamine compounds. Alcohols such as, for example, methanol, ethanol or propanol may also be employed in this reaction.

The substitution reaction between such a nucleophilic compound and a compound of formula [I] is normally conducted in a solvent. As said solvent, water may be mentioned as the commonest solvent, although a mixture of water and a reaction-inert hydrophilic solvent, e.g. acetone, acetonitrile, tetrahydrofuran, dimethylformamide, methanol, ethanol, dimethylsulfoxide or the like, may likewise be employed. The reaction may also be conducted even in a non-aqueous system. While compound [I] may be a free compound, it is more appropriate to react [I] in the form of an alkali metal salt, e.g. the salt of sodium, potassium or the like, or an organic amine salt, e.g. the salt of triethylamine, trimethylamine or the like. The nucleophilic compound, too, is reacted either in the free form or as an alkali metal salt or organic amine salt. The proper amount of said nucleophilic compound used in the reaction is not less than one equivalent based on compound [I]. While it depends upon the types of nucleophilic compound and compound [I], this reaction is preferably conducted generally under weakly acid to weakly alkaline conditions in cases where an aqueous solvent is employed. While the reaction temperature depends largely upon the nature of compound [I] and cannot be specified in general terms, it is preferably within the range of 10° C. to 70° C. It is also possible to accomplish a direct synthesis of [III] by causing the nucleophilic reagent to be present concomitantly in the reaction system of [II] and [IV]. The reaction time cannot be specified in general terms, either, for it depends upon the reaction temperature, pH, type of nucleophilic reagent and other factors. Roughly speaking, however, the reaction goes to completion in 30 minutes to 2 hours when the reaction temperature is 60° C. The reaction may also be carried out in the presence of, as added to the reaction system, an inorganic salt, e.g. the chloride, bromide, iodide, thiocyanide or nitrate of lithium, sodium, potassium, ammonium or the like. At any event, the feasibility of the nucleophilic substitution reaction at such a low temperature and in a non-aqueous phase prevents decomposition of compound [I] and permits synthesis of the compound which cannot be synthesized in an aqueous phase. Where [I] has a high activity such that it will be readily substituted by a nucleophilic reagent at room temperature, for example in the case of an isatin derivative, [I] need not be isolated, but [III] may be directly synthesized by allowing a nucleophilic compound to be present in the reaction system when [II] is reacted with [IV].

The compound [I] wherein $R^1$ is an acyl group can be converted to the corresponding compound wherein $R^1$ is hydrogen by cleaving the 7-acyl group off in a manner conventional per se (e.g any of the procedures set forth in Japanese Patent Publication No.13862/1966 and No.40899/1970, Japanese Patent Application As Laid Open No.34387/1972, No. 95292/1975 and No.96591/1975, Japanese Patent Publication No.35079/1975 or United States Patent No. 3632578).

Into this compound may be introduced a compound which has previously been mentioned by way of example for $R^1$ as the 6- or 7-substituents of penicillin or cephalosporin compounds, by previously activating the same in a known manner. Thus, for example, the compound wherein $R^1$ is 4-halogeno-3-oxobutyryl can be obtained by reacting the said compound with a 4-halogeno-3-oxobutyryl halide which, in turn, may be reacted with thiourea to produce the 7-[2-(2-imino-4-thiazolin-4-yl)acetamido]-compound. While it depends somewhat on the type of 3-substituent, these compounds invariably display excellent antibiotic activity. For example, the compound with 1-methyltetrazol-5-ylthiomethyl in 3-position is particularly useful, approximately the same effect being accomplished with this compound at a dose about one-fifth that of cefazolin.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g", "mg", "ml", "cm", "Hz", "DMSO", "arom" and "decomp." are abbreviations of "gram", "milligram", "milliliter", "centimeter", "Herz", "dimethylsulfoxide", "aromatic" and "decomposed", respectively. Resins named "Amberlite" are products manufactured by Rohm & Haas Co. in U.S.A. "Celite" and "Sephadex" are marketed by Johns-Manville Sales Corp. and Pharmacia A.B., respectively. All the temperatures are uncorrected and the percentages are all on the weight basis except those specifically defined. The NMR spectra were measured using a Varian Model HA 100 (100 MHz) or T60 (60 MHz) spectrometer with tetramethylsilane as the internal reference and all $\delta$ values are in ppm. The symbols "s" stands for a singlet, "d" a doublet, "t" a triplet, "q" a quarter; "m" a multiplet, and "J" a coupling constant.

EXAMPLE 1

In N,N-dimethylformamide (80 ml) is suspended deacetylcephalosporin C sodium monohydrate (purity 90%, 20 g) and, with the addition of concentrated hydrochloric acid (8 ml), the suspension is stirred under ice-cooling for 15 minutes. To this solution is added N,N-dimethylformamide (80 ml), followed by addition of N-carboethoxyphthalimide (40 g) and triethylamine (40 ml) in the order mentioned. The mixture is stirred at room temperature for 3 hours. While stirring it under ice-cooling, this reaction mixture is poured in 0.42% hydrochloric acid (2.0 l), followed by the addition of sodium chloride (380 g). The mixture is stirred for 30 minutes. The resultant precipitate is recovered by filtration, rinsed with a saturated aqueous solution of sodium chloride and dried over phosphorus pentoxide under reduced pressure. The product is suspended in ethyl acetate (1.2 l) and stirred at room temperature for 30 minutes. The insoluble fraction is removed by filtration and, under stirring, toluene (500 ml) is gently added. The mixture is concentrated under reduced pressure (to 500 ml) and the precipitate is recovered by filtration, rinsed with toluene and dried under reduced pressure. The procedure provides 7β-(D-5-phthalimido-5-carboxyvaleramido)-3-[2-(N-carboethoxycarbamoyl)benzoyloxy]methyl-3-cephem-4-carboxylic acid (31 g).

IR(KBr): cm$^{-1}$ 1771, 17155

NMR(d$_6$-DMSO): δ 1.17(3H, t, J=7 Hz, OCH$_2$CH$_3$), 1.2-2.4(6H, m- —(CH$_2$)$_3$—), 3.56(2H, ABq, J=18 Hz, 2—CH$_2$), 4.05(2H, q, J=7 Hz, —OCH$_2$CH$_3$), 4.74(1H, t, J=7 Hz,

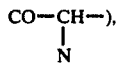

5.07(1H, d, J=5 Hz, 6-H), 5.08(2H, ABq, J=13 Hz, 3—CH₂O—), 5.65(1H, q, J=5 & 8 Hz, 7-H), 7.36–7.94(8H, m, arom-H), 8.80(1H, d, J=8 Hz, 7—CONH—), 11.08(1H, —CONH—CO—)

EXAMPLE 2

In cold water (100 ml) is suspended 7β-(D-5-phthalimido-5-carboxyvaleramido)-3-[2-(N-carboethoxycarbamoyl)benzoyloxy]methyl-3-cephem-4-carboxylic acid (16.5 g), followed by the addition of 5-mercapto-1-methyl-1H-tetrazole (4.2 g). Then, under ice-cooling and stirring, sodium hydrogen carbonate (6.0 g) is added in small installments. To the resultant clear solution is added a further small amount of sodium hydrogen carbonate and, after adjustment to pH 5.0, sodium chloride (30 g) is added. The mixture is heated at 60° C. for 1.5 hours. To this reaction mixture is added water (100 ml) and, under stirring, the mixture is adjusted to pH 1.5 with dilute hydrochloric acid. The resultant precipitate is recovered by filtration, rinsed with a saturated aqueous solution of sodium chloride and dried over phosphorus pentoxide under reduced pressure. The procedure provides 7β-(D-5-phthalimido-5-carboxyvaleramido)-3-(1-methyl-1H-tetrazol-5-yl)thiomethyl-3-cephem-4-carboxylic acid (13.0 g).

IR(KBr): cm$^{-1}$ 3325, 1780, 1730, 1715, 1650, 1545

NMR(d₆-DMSO): δ 1.40–1.76(2H, m), 2.0–2.4(4H, m), 3.64(2H, ABq, J=19 Hz, 2—CH₂), 3.93(3H, s, —NCH₃), 4.30(2H, ABq, J=15 Hz, 3—CH₂), 4.73(1H, t, J=8 Hz,

5.01(1H, d, J=5 Hz, 6-H), 5.62(1H, dd, J—5 & 9 Hz, 7-H), 7.85(4H, s, arom-H), 8.80(1H, d, J=9 Hz, —CONH)

EXAMPLE 3

In N,N-dimethylformamide (0.4 l) is suspended deacetylcephalosporin C sodium monohydrate (purity 90%, 100 g) and, with the addition of concentrated hydrochloric acid (0.04 l), the suspension is stirred for 30 minutes. To this reaction mixture is added N,N-dimethylformamide (0.3 l) and, then, N-carboethoxyphthalimide (200 g) and triethylamine (0.2 l) are added in the order mentioned. The mixture is stirred at room temperature for 3 hours. This reaction mixture is poured in an ice-cooled mixture of ethyl acetate (1.5 l), concentrated hydrochloric acid (120 ml) and 14% aqueous sodium chloride (2.0 l), followed by stirring for 20 minutes. The ethyl acetate layer is taken and the aqueous layer is extracted with ethyl acetate. The ethyl acetate extracts are pooled and rinsed with 14% aqueous sodium chloride. To this ethyl acetate solution is gently added a 4.75% aqueous solution of sodium hydrogen carbonate (10 l), followed by stirring for 15 minutes. The aqueous layer is taken and, following addition of sodium chloride (300 g) and with stirring, a mixture of 5-mercapto-1-methyl-1H-tetrazole (32 g), sodium hydrogen carbonate (17 g) and water (0.12 l) is added. Then, the mixture is adjusted to pH 4.7 with a small amount of sodium hydrogen carbonate, followed by stirring at 60° C. for 1.5 hours. From the reaction mixture, the ethyl acetate is distilled off under reduced pressure. Following the addition of water (2.5 l), the mixture is adjusted to pH 1.5 with diluted hydrochloric acid and the resultant precipitate is recovered by filtration, rinsed with a saturated aqueous solution of sodium chloride and dried over phosphorus pentoxide under reduced pressure. The procedure provides 7β-(D-5-phthalimido-5-carboxyvaleramido)-3-(1-methyl-1H-tetrazol-5-yl)thiomethyl-3-cephem-4-carboxylic acid (139 g). In IR and NMR spectra, this product is in good agreement with the product obtained in Example 2.

EXAMPLE 4

In N,N-dimethylformamide (40 ml) is dissolved 7β-(2-thienylacetamido)-3-hydroxymethyl-3-cephem-4-carboxylic acid sodium salt (3.8g), and following the addition of N-carboethoxysaccharin (4.0 g) and triethylamine (2 ml), the solution is stirred at room temperature for 4 hours. The reaction mixture is poured in water (100 ml) and rinsed with ethyl acetate (40 ml). The aqueous layer is adjusted to pH 2.0 with diluted phosphoric acid and extracted with a saturated aqueous solution of sodium chloride. The solution is dried over magnesium sulfate and concentrated. Then, upon addition of ether, 7β-(2-thienylacetamido)-3-[2-(N-carboethoxysulfamoyl)benzoyloxy]methyl-3-cephem-4-carboxylic acid crystallizes with one mole of ether.

Yield 3.8 g.

IR(KBr): cm$^{-1}$ 1790, 1748, 1698, 1652

NMR(d₆-DMSO): δ 1.0–1.2(9H, m, —COOCH₂C$\underline{H}$₃ & (C$\underline{H}$₃CH₂)₂O), 3.35(4H, q, (CH₃C$\underline{H}$₂)₂O), 3.63(2H, broad, 2—CH₂), 3.75 (2H, s, —C$\underline{H}$₂CONH—), 4.01(2H, q, —COOC$\underline{H}$₂CH₃), 5.07(1H, d, J=5 Hz, 6-H), 5.13(2H, ABq, J=13 Hz, 3—CH₂), 5.70(b 1H, dd, J=5 & 8 Hz, 7-H),

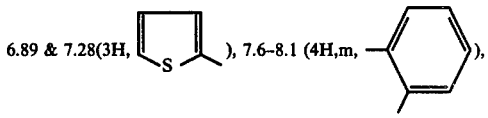

9.07(1H, d, J=8 Hz, —CONH—)

EXAMPLE 5

The reaction of Example 4 is repeated using 7β-phenylacetamido-3-hydroxymethyl-3-cephem-4-carboxylic acid sodium salt (3.7 g) in place of 7β-(2-thienylacetamido)-3-hydroxymethyl-3-cephem-4-carboxylic acid sodium salt. This procedure provides crystals of 7β-phenylacetamido-3-[2-(N-carboethoxysulfamoyl)benzoyloxy]methyl-3-cephem-4-carboxylic acid-ether(one mole). Yield 4.0 g.

IR(KBr): cm$^{-1}$ 1794, 1750, 1701, 1650

NMR(d₆-DMSO): δ 1.0–1.2(9H, m, —COOCH₂C$\underline{H}$₃ & (C$\underline{H}$₃CH₂)₂O), 3.35(4H, q, (CH₃C$\underline{H}$₂)₂O), 3.52(2H, —C$\underline{H}$₂CO—), 3.62(2H, broad, 2—CH₂), 4.01(2H, q, —COOC$\underline{H}$₂CH₃), 5.05(1H, d, J=5 Hz, 6-H), 5.17(2H, ABq, J=13 Hz, 3—CH₂), 5.69(1H, dd, J=5 & 8 Hz, 7-H),

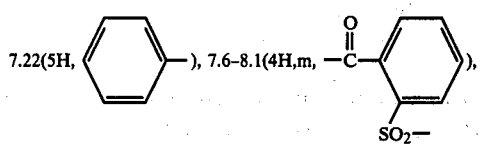

7.22(5H, ⟨⟩—), 7.6–8.1(4H, m, —C(=O)—⟨⟩—SO₂—), 9.05(1H, d, J=8 Hz —CONH)

Analysis: $C_{30}H_{35}N_3O_{11}S_2$ Calcd.(%): C, 53.17; H 5.21; N, 6.20; S, 9.46; Found (%): C, 53.20; H, 5.34; N, 6.23; S, 9.65.

EXAMPLE 6

In water (50 ml) is suspended 7β-phenylacetamido-3-[2-(N-carboethoxysulfamoyl)benzoyloxy]methyl-3-cephem-4-carboxylic acid (3.0 g) together with 5-mercapto-1-methyl-1H-tetrazole (1.0 g). The mixture is adjusted to pH 5.5 with sodium hydrogen carbonate and the resultant solution is heated at 60° C. for 50 minutes. The solution is brought to pH 2.0 with dilute phosphoric acid and extracted with ethyl acetate (100 ml). The extract is rinsed with a saturated aqueous solution of sodium chloride, dried and concentrated. Then, following the addition of ether, the precipitate is recovered by filtration. By the above procedure is obtained 7β-phenylacetamido-3-(1-methyl-1H-tetrazol-5-yl)thiomethyl-3-cephem-4-carboxylic acid (1.8 g).

IR(KBr): cm⁻¹ 3270, 1785, 1733, 1662, 1628, 1542

NMR(d₆-DMSO): δ 3.55(2H, s,

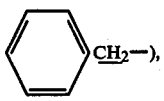

3.60(2H, broad, 2—CH₂), 3.92(3H, s, —N—CH₃), 4.26(2H, broad, 3—CH₂—), 5.00(1H, d, J=5 Hz, 6-H), 5.60(1H, q, J=5 & 8 Hz, 7-H), 7.23(5H, s), 8.98(1H, d, J=8 Hz, —CONH)

EXAMPLE 7

In N,N-dimethylformamide (40 ml) is dissolved 7β-(2-thienylacetamido)-3-hydroxymethyl-3-cephem-4-carboxylic acid sodium salt (3.8 g), followed by the addition of N-tosylphthalimide (4.0 g) and triethylamine (2.0 ml) in that order. The mixture is stirred at room temperature for 4 hours. The reaction mixture is poured in water (100 ml) and rinsed with ethyl acetate. The aqueous layer is adjusted to pH 2.0 with dilute phosphoric acid and extracted with ethyl acetate. The extract is dried and, then, a solution of sodium 2-ethylhexanoate in isopropyl alcohol is added. By this procedure is obtained 7β-(2-thienylacetamido)-3-[2-(N-tosylcarbamoyl)benzoyloxy]methyl-3-cephem-4-carboxylic acid sodium salt (4.0 g).

IR(KBr): cm⁻¹ 1769, 1695, 1620

NMR(d₆-DMSO): δ 2.27(3H, s, —CH₃), 3.48(2H, broad, 2—CH₂), 3.74(2H, s, CH₂CONH), 4.97(1H, d, 6-H), 5.00(2H, ABq, J=13 Hz, 3—CH₂), 5.58(1H, q, J=5 & 8 Hz, 7-H), 6.8–7.9(11H, m), 9.02(1H, d, J=8 Hz, 7—CONH)

EXAMPLE 8

In N,N-dimethylformamide (10 ml) is dissolved 7β-(D-5-phthalimido-5-carboxyvaleramido)-3-hydroxymethyl-3-cephem-4-carboxylic acid sodium salt (1.3 g), followed by the addition of N-carboethoxysaccharin (0.8 g) and triethylamine (0.4 ml). The mixture is stirred at room temperature for 4 hours. It is then poured in water (50 ml) and rinsed with ethyl acetate. The aqueous layer is adjusted to pH 2.0 with dilute phosphoric acid and extracted with ethyl acetate. The extract is dried and concentrated, followed by addition of ether. By this procedure is obtained 7β-(D-5-phthalimido-5-carboxyvaleramido)-3-[2-(N-carboethoxysulfamoyl)benzoyloxy]methyl-3-cephem-4-carboxylic acid (1.4 g) as a powder.

NMR(d₆-DMSO): δ 1.10(3H, t, CH₂CH₃), 1.3–2.4(6H, m, —(CH₂)₃—), 3.60(2H, broad, 2—CH₂), 4.01(2H, q, CH₂CH₃), 4.73(1H, t, J=7 Hz,

—CH—),
 |
 N 5.03(1H, d, J=5 Hz, 6-H), 5.15(2H, ABq, J=13 Hz, 3—CH₂), 5.65(1H, q, J=5 & 8 Hz, 7-H), 7.48–8.1(8H, m), 8.75(1H, d, J=8 Hz, —CONH—)

EXAMPLE 9

In water (8 ml) is added 7β-(D-5-phthalimido-5-carboxyvaleramido)-3-[2-(N-carboethoxysulfamoyl)benzoyloxy]methyl-3-cephem-4-carboxylic acid (0.8 g), which is then dissolved by the addition of sodium hydrogen carbonate. Then, 5-mercapto-1-methyl-1H-tetrazole (0.15 g) is added, followed by addition of a further amount of sodium hydrogen carbonate to adjust to pH 5.3. The mixture is heated on a water bath at 60° C. for 50 minutes, after which time it is brought to pH 2.0 with dilute phosphoric acid and extracted with ethyl acetate (20 ml). The extract is dried and concentrated, followed by the addition of ether to the residue. By the above procedure is obtained 7β-(D-5-phthalimido-5-carboxyvaleramido)-3-(1-methyl-1H-tetrazol-5-yl)thiomethyl-3-cephem-4-carboxylic acid (0.6 g). In NMR spectrum, this product is in good agreement with the product obtained in Example 2.

EXAMPLE 10

In a mixture of N,N-dimethylformamide (16 ml) and water (4 ml) is dissolved 7β-(D-5-benzamido-5-carboxyvaleramido)-3-hydroxymethyl-3-cephem-4-carboxylic acid disodium salt (2.6 g), followed by the addition of N-tosylphthalimide (2.3 g) and triethylamine (0.7 g). The mixture is stirred at room temperature for 2 hours. The reaction mixture is poured in water, rinsed with ethyl acetate, adjusted to pH 2.0 with dilute phosphoric acid and extracted with ethyl acetate. After drying, the solvent is distilled off and the resultant residue is made into a powder by a rinse with ether. By the above procedure is obtained 7β-(D-5-benzamido-5-carboxyvaleramido)-3-[2-(N-tosylcarbamoyl)benzoyloxy]methyl-3-cephem-4-carboxylic acid (3.5 g).

IR(KBr): cm⁻¹ 1780, 1725

NMR(d₆-DMSO): δ 1.5–2.5(6H, m, —(CH₂)₃—), 2.34(3H, s, —CH₃), 3.48(2H, ABq, J=18 Hz, 2—CH₂), 4.36(1H, broad,

4.93(2H, ABq, J=13 Hz, 3—CH$_2$), 5.01(1H, d, J=5 Hz, 6-H), 5.64(1H, q, J=5 & 8 Hz, 7-H), 7.2–8.0(13H, m, arom-H), 8.51(1H, d, J=8 Hz, —CONH—), 8.79(1H, d, J=8 Hz, —CONH—)

EXAMPLE 11

With the addition of sodium hydrogen carbonate, 7β-(D-5-benzamido-5-carboxyvaleramido)-3-[2-(N-tosylcarbamoyl)benzoyloxy]methyl-3-cephem-4-carboxylic acid (1.6 g) is dissolved in water (20 ml), followed by the addition of a further amount of sodium hydrogen carbonate to adjust the solution to pH 5.2. The solution is heated at 60° C. for 50 minutes and, after cooling, the mixture is diluted with a saturated aqueous solution of sodium chloride (40 ml) and adjusted to pH 1.5 with dilute hydrochloric acid. The resultant solid precipitate is recovered by filtration, rinsed with a saturated aqueous solution of sodium chloride and dissolved in a mixture of ethyl acetatetetrahydrofuran (2:1)(40 ml) and water (10 ml). After separation, the organic layer is dried and the solvent is distilled off. The residue is rinsed with ether to obtain a powder. By the above procedure is obtained 7β-(D-5-benzamido-5-carboxyvaleramido)-3-(1-methyl-1H-tetrazol-5-yl)thiomethyl-3-cephem-4-carboxylic acid (1.1 g).

IR(KBr): cm$^{-1}$ 3340, 1783, 1730, 1645, 1535

NMR(d$_6$-DMSO): δ 1.50–2.0(4H, m), 2.05–2.45(2H, m), 3.70(2H, broad), 3.93(3H, s), 4.15–4.55(3H, m), 5.10(1H, d, J=5 Hz), 5.66(1H, q, J=5 & 9 Hz), 7.32–7.97(5H, m), 8.43(1H, d, J=8 Hz), 8.73(1H, d, J=9 Hz)

EXAMPLE 12

In N,N-dimethylformamide (30 ml) is dissolved 7β-(2-thienylacetamido)-3-hydroxymethyl-3-cephem-4-carboxylic acid sodium salt (3.8 g), followed by addition of N-carboethoxysuccinimide (2.5 g) and triethylamine (1.5 ml). The mixture is stirred at room temperature for 20 hours. The reaction mixture is poured in ice-water and rinsed with ethyl acetate (50 ml). The aqueous layer is adjusted to pH 2.0 with diluted phosphoric acid, extracted with ethyl acetate and dried. Then, a solution of sodium 2-ethylhexanoate in isopropyl alcohol is added. The precipitate is 7β-(2-thienylacetamido)-3-[3-(N-carboethoxycarbamoyl)propionyloxy]methyl-3-cephem-4-carboxylic acid sodium salt (32 g).

NMR(D$_2$O): δ 1.33(3H, t, CH$_3$—), 2.80(4H, broad, —(CH$_2$)$_2$—), 3.44 (2H, ABq, J=18 Hz, 2—CH$_2$), 3.81(2H, s, —CH$_2$CO—), 4.25(2H, q, —CH$_2$—), 5.07(1H, d, J=5 Hz, 6-H), 5.70(1H, d, J=5Hz, 7-H), 7.0–7.4(3H, 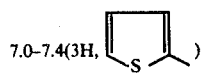 )

EXAMPLE 13

In acetonitrile (10 ml) is dissolved 7β-(D-5-phthalimido-5-carboxyvaleramido)-3-hydroxymethyl-3-cephem-4-carboxylic acid ditriethylamine salt (705 mg), followed by the addition of triethylamine (202 mg), 5-mercapto-1-methyl-1H-tetrazole (232 mg) and N-carboethoxyisatin (438 mg) in the order mentioned. The reaction is carried out at room temperature for 3 hours, after which time the solvent is distilled off under reduced pressure. The residue is dissolved in water-ethyl acetate, adjusted to pH 2.0 and extracted with ethyl acetate. The ethyl acetate solution is rinsed with water and, following the addition of water, is adjusted to pH 5.0 with an aqueous solution of sodium hydrogen carbonate. After separation, the aqueous solution is concentrated and the residue is subjected to column chromatography on Amberlite XAD-2. Elution is carried out with a mixture of water-methanol and the eluate is freeze-dried. By the above procedure is obtained 7β-(D-5-phthalimido-5-carboxyvaleramido)-3-(1-methyl-1H-tetrazol-5-yl)thiomethyl-3-cephem-4-carboxylic acid monosodium salt (512 mg).

IR(KBr): cm$^{-1}$ 1768, 1710, 1665, 1610, 1535

NMR(D$_2$O): δ 1.30–2.60(6H, m), 3.34(2H, ABq, J=20 Hz, 2—CH$_2$), 3.99(3H, s, N—CH$_3$), 4.10(2H, ABq, J=14 Hz, 3—CH$_2$), 4.50(1H, broad), 4.97(1H, d, J=5 Hz, 6-H), 5.53(1H, d, J=5Hz, 7-H), 7.86(4H, s, arom-H)

EXAMPLE 14

In DMF (10 ml) is dissolved 7β-phenylacetamido-3-hydroxymethyl-3-cephem-4-carboxylic acid triethylamine salt (900 mg), followed by the addition of triethylamine (0.4 ml) and N-carboethoxyisatin (876 mg). The mixture is stirred at room temperature for 2 hours, after which time the DMF is distilled off under reduced pressure.

Following the addition of water and ethyl acetate, the residue is adjusted to pH 2.0. The aqueous layer is taken, adjusted to pH 4.0 with an aqueous solution of sodium hydrogen carbonate and subjected to column chromatography on Dowex 1×2 (AcO$^-$) and the resultant aqueous solution is freeze-dried. By this procedure is obtained N-(7β-phenylacetamido-3-cephem-3-ylmethyl)triethylammonium-4-carboxylate (620 mg).

IR(KBr): cm$^{-1}$ 1775, 1665, 1615, 1545, etc.

NMR(D$_2$O): δ 1.29(9H, t, J=6 Hz), 2.65–4.25(12H, m), 4.55(1H, broad), 5.08(1H, d, J=5 Hz, 6-H), 5.62(1H, d, J=5 Hz, 7-H), 7.25(5H, s, arom-H)

EXAMPLE 15

In dimethylformamide (4.0 ml) is suspended deacetylcephalosporin C sodium monohydrate (purity 90%, 826 mg), and under cooling with ice, concentrated hydrochloric acid (0.33 ml) is added. To the resultant clear solution is added DMF (8.0 ml) together with triethylamine (2.1 ml) and 5-mercapto-1-methyl-1H-tetrazole (464 mg). Then, at room temperature, N-carboethoxyisatin (1.752 g) is added in small installments. Thereafter, the reaction is conducted at room temperature for 4 hours. After the reaction is completed, the DMF is distilled off under reduced pressure. Following the addition of water and ethyl acetate, the residue is adjusted to pH 2.0. The ethyl acetate layer is separated and diluted with water and adjusted to pH 7.0 with an aqueous solution of sodium hydrogen carbonate. After separation, the aqueous solution is concentrated and subjected to column chromatography on Amberlite XAD-2. Elution is carried out with a solvent mixture of water and methanol and the eluate is freeze-dried. By the above procedure is obtained 7β-[D-5-(2-ethoxycarbonylamino)-phenylglyoxamido-5-carboxyvaleramido]-3-(1-methyl-1H-tetrazol-5-yl)thiomethyl-3-cephem-4-carboxylic acid disodium salt (1.051 g).

IR(KBr): cm$^{-1}$ 1765, 1745, 1665, 1645, 1607, 1590, 1530

NMR(D$_2$O): δ 1.20(3H, t, J=8 Hz), 1.40–2.15(4H, m), 2.20–2.60 (2H, m), 3.43(2H, ABq, J=18 Hz, 2—CH$_2$), 3.88(3H, s, N—CH$_3$), 3.75–4.50(5H, m), 5.04(1H, d, J=5 Hz, 6-H), 5.56(1H, d, J=5 Hz, 7-H), 7.05–8.05(4H, m, arom-H)

EXAMPLE 16

(1) A mixture of dichloromethane (300 ml), triethylamine (27 ml) and dimethylaniline (100 ml) is previously cooled to 10° C. and, then, 7-[D-5-(phthalimido-5-carboxy valeramido]-3-(1-methyl-1H-tetrazol-5-yl)thiomethyl-3-cephem-4-carboxylic acid (50 g) is added and dissolved. Then, upon addition of dichlorodimethylsilane (36 ml), the internal temperature increases to 27° C. The mixture is stirred at this temperature for 30 minutes, after which time it is cooled to an internal temperature of −35° C. Then, phosphorus pentachloride (32.4 g) is added. The mixture is stirred at −25° C. for 40 minutes and, then, at −35° C., thioacetamide (20 g) is added. The mixture is stirred at −20°—−25° C. for 40 minutes and, then, at −30° C., methanol (200 ml) is gently added dropwise. Then, at the same temperature, sulfur monochloride (17 ml) is gently added dropwise. The mixture is stirred for 20 minutes, after which time water (200 ml) was added. It is then adjusted to pH 3.2 with 40% aqueous potassium carbonate solution and stirred for 60 minutes. The resultant crystals are recovered by filtration and rinsed with water and acetone. The crude crystals thus obtained are suspended in 10% hydrochloric acid (230 ml) and stirred at 30° C. for 1 hour. The insolubles are filtered off and, after cooling to 5°–10° C., the filtrate is adjusted to pH 3.3 with potassium carbonate, followed by stirring for 1 hour. The resultant crystals are recovered by filtration, rinsed with water and acetone, and dried over phosphorus pentoxide. By the above procedure is obtained 7-amino-3-(1-methyltetrazol-5-yl)thiomethyl-3-cephem-4-carboxylic acid (17.0 g)

IR(KBr): 1795 cm$^{-1}$

NMR(in D$_2$O+NaHCO$_3$): δ 3.61 & 3.98(Abq, J=18 Hz, 2—CH$_2$), 4.21(s, tetrazole —CH$_3$), 5.21(d, J=4.5 Hz, 6-H), 5.60 (d, J=4.5 Hz, 7-H)

(2) Chlorine gas (2.8 g) is bubbled through a solution of diketene (3.3 g) in methylene chloride (160 ml) under cooling and stirring to maintain the internal temperature at −25°—−35° C. over a period of 100 minutes, after which time the mixture is further stirred at that temperature for 30 minutes. Separately, 7-amino-3-(1-methyltetrazol-5-yl)-thiomethyl-3-cephem-4-carboxylic acid (10.0 g) and dibutylamine (7.9 g) are dissolved in methylene chloride (60 ml) and the solution is cooled to −10° C.

To this is added dropwise the above reaction mixture over a period of 30 minutes, with cooling and stirring to maintain the temperature of the solution at −10° C. to −20° C. Then, the mixture is further stirred at that temperature for 40 minutes.

Thin-layer chromatography of this reaction mixture demonstrates the presence of 7β-(4-chloro-3-oxobutyrylamido)-3-(1-methyltetrazol-5-yl)thiomethyl-3-cephem-4-carboxylic acid. In this reaction mixture is dissolved thiourea (4.64 g) and the internal temperature is gradually increased to 17° to 19° C. Then, the mixture is stirred at that temperature, whereupon crystals separates. These crystals are collected by suction-filtration, rinsed with methylene chloride (30 ml) and dried. By the above procedure is obtained 2-(2-imino-4-thiazolin-4-yl)acetamido-3-(1-methyltetrazol-5-yl)thiomethyl-3-cephem-4-carboxylic acid. (Melting point: 176°–180° C. (decomp.)

IR(KBr): cm$^{-1}$ 1762, 1662

NMR(d$_6$-DMSO) δ 3.39(s, CH$_2$CO) 3.55 & 3.77(ABq, J=18 Hz, 2—CH$_2$), 3.90(s, tetrazole 1—CH$_3$), 4.21 & 4.36(ABq, J=14 Hz,) 3—CH$_2$), 5.03(d, J=5 Hz, 6-H), 5.66(dd, J=9 & 5 Hz, 7-H), 6.23(s, thiazoline 5-H), 6.2–7.1(m, NHX2), 8.85(d, J=9 Hz, CONH)

EXAMPLE 17

In acetonitrile (14 ml) is dissolved 7β-phenylacetamido-3-hydroxymethyl-3-cephem-4-carboxylic acid triethylamine salt (900 mg), followed by the addition of triethylamine (200 mg), 5-mercapto-1-methyl-1H-tetrazole (464 mg) and N-(methylcarbamoyl)isatin (916 mg). The mixture is stirred at 30° C. overnight. The solvent is then distilled off and the residue is dissolved by the addition of water and ethyl acetate. After separation, the water layer is taken, rinsed once with ethyl acetate and rendered acidic with hydrochloric acid. Following the addition of ethyl acetate, the mixture is stirred for 30 minutes. After separation, the organic layer is taken and rinsed with an aqueous solution of sodium chloride. It is extracted with an aqueous solution of sodium hydrogen carbonate. The water layer is purified by column chromatography on Sephadex LH-20. The fractions rich in the contemplated compound are pooled, concentrated, rendered acidic with phosphoric acid and extracted with ethyl acetate. After drying, the extract is concentrated, followed by addition of ether to the residue. The procedure provides 7β-phenylacetamido-3-(1-methyl-1H-tetrazol-5-yl)thiomethyl-3-cephem-4-carboxylic acid. The NMR spectrum of this product is in good agreement with that of the compound obtained in Example 6.

EXAMPLE 18

In dichloromethane (100 ml) is dissolved triethylamine 7β-phenylacetamido-3-hydroxymethyl-3-cephem-4-carboxylate (4.5 g), followed by the addition of triethylamine (1.4 ml) and N-carboethoxysaccharin (3.0 g). The mixture is stirred at room temperature overnight. The solvent is distilled off under reduced pressure and the residue is stirred with water and ethyl acetate. After separation, the water layer is taken, rendered acidic with phosphoric acid and extracted with ethyl acetate. After drying, the solvent is distilled off, followed by addition of ether to the residue. The above procedure provides crystals (6.0 g). This product is in good agreement with the product obtained in Example 4 in infrared spectrum.

EXAMPLE 19

In N,N-dimethylformamide (40 ml) is dissolved disodium 7β-[D-5-(p-t-butylbenzamido)-5-carboxyvaleramido]-3-hydroxymethyl-3-cephem-4-carboxylate (5.2 g) and, under cooling with ice, N-carboethoxysaccharin (3.2 g) and triethylamine (1.6 ml) are added. The mixture is stirred at room temperature for 2 hours. The reaction mixture is poured in icewater and rinsed twice with ethyl acetate. The water layer is adjusted to pH 2.0 and extracted with ethyl acetate. The organic layer is rinsed twice with water, dried over sodium sulfate and concentrated. Following the addition of ether, the solution is cooled with ice and the resultant precipitate is recovered by filtration. By the above procedure is obtained 7β-[D-5-(p-t-butylbenzamido)-5-carboxyvaleramido]-3-[2-(N-carboethoxysulfamoyl)benzoyloxy]-methyl-3-cephem-4-carboxylic acid (5.3 g).

NMR($d_6$-DMSO): δ 1.09(3H, t, —CH$_2$C$\underline{H}_3$), 1.5–2.5(6H, m), 3.61(2H, broad, 2—CH$_2$), 3.99(2H, q, —C$\underline{H}_2$CH$_3$), 4.35(1H, broad, —CH—), 4.99 & 5.32 (2H, ABq, J=13 Hz, 3—CH$_2$), 5.05(1H, d, J=5 Hz, 6-H), 5.66(1H, dd, J=5 & 8,7-H), 7.3–8.1(8H, m), 8.42(1H, d, —CONH—), 8.78(1H, d, —CONH—)

EXAMPLE 20

In dichloromethane (120 ml) is suspended 7β-(D-5-phthalimido-5-carboxyvaleramido)-3-[2-(N-carboethoxycarbamoyl)-benzoyloxy]methyl-3-cephem-4-carboxylic acid (14.5 g) and, at a temperature not exceeding 10° C., the suspension is dissolved by the addition of triethylamine (12 ml). Following the addition of N,N-dimethylaniline (20 ml) and dimethyldichlorosilane (8.9 ml), the mixture is stirred at 20°–25° C. for 30 minutes. After cooling to −30° C., phosphorus pentachloride (9.85 g) is added. The reaction is conducted at −25° C. for 30 minutes and, then, at a temperature not exceeding −20° C., methanol (50 ml) is added dropwise. Then, at −15°–−10° C., the reaction is further carried out for 20 minutes. Following the addition of ice-water (100 ml), the mixture is stirred for 5 minutes. The reaction mixture is separated and the water layer is taken, rinsed with dichloromethane and brought to pH 3.5 with 40% aqueous potassium carbonate solution. The precipitate is recovered by filtration, rinsed with water, 50% water-methanol and acetone. By the above procedure is obtained 7β-amino-3-[2-(N-carboethoxycarbamoyl)-benzoyloxy]-methyl-3-cephem-4-carboxylic acid.

IR(KBr): cm$^{-1}$ 1780, 1723

NMR($D_2O$+NaOD): δ 1.30(3H, t, CH$_2$C$\underline{H}_3$), 3.54(2H, ABq, J=18 Hz, 2—CH$_2$), 4.25(2H, q, —C$\underline{H}_2$CH$_3$), 7.4–8.2(4H, m, arom-H)

EXAMPLE 21

(1) In dimethylformamide (20 ml) is dissolved sodium 7β-(t-butoxycarbonyl)amino-3-hydroxymethyl-3-cephem-4-carboxylate (3.20 g), followed by the addition of N-carboethoxysaccharin (3.20 g) and triethylamine (2.0 ml). The solution is stirred for one hour at room temperature and, after the addition of triethylamine (2.0 ml), stirred further for one hour. The solution is poured into toluene (1 L) and the resultant precipitate is collected by filtration, washed with toluene and dried. The powder thus obtained is dissolved in water (30 ml). After the addition of ethyl acetate (200 ml), the solution is adjusted to pH 4.0 with diluted phosphoric acid. After separation, the ethyl acetate solution is washed with water, dried over anhydrous sodium sulfate and concentrated. To the concentrate (30 ml), ether (200 ml) is added under stirring and the resultant precipitate is filtered off. The filtrate is concentrated under reduced pressure and to the concentrate (30 ml) is added carbon tetrachloride (100 ml). The resultant precipitate is collected by filtration, washed with carbon tetrachloride and dried over phosphorus pentoxide. The procedure provides 7β-(t-butoxycarbonyl)amino-3-[2-(N-carboethoxysulfamoyl)benzoyloxy]methyl-3-cephem-4-carboxylic acid (2.50 g).

IR(KBr): cm$^{-1}$ 3400–3250, 1790 1733

NMR($d_6$-DMSO): δ 1.12(3H, t, J=7 Hz, —CH$_2$C$\underline{H}_3$), 1.42(9H, s, —C(CH$_3$)$_3$), 3.62(2H, broad, 2—CH$_2$), 4.03(2H, q, J=7 Hz, —C$\underline{H}_2$CH$_3$), 5.05 (1H, d, J=5 Hz, 6-H), 5.18(2H, ABq, J=13 Hz, 3—CH$_2$), 5.48(1H, q, J=5 & 8 Hz, 7-H), 7.57–8.11(4H, m, arom-H)

(2) 7β-(t-Butoxycarbonyl)amino-3-[2-(N-carboethoxysulfamoyl)benzoyloxy]methyl-3-cephem-4-carboxylic acid (2.2 g) is dissolved in ice cooled solution of trifluoroacetic acid (20 ml) and the mixture is stirred for 20 minutes. Then, trifluoroacetic acid is taken off under reduced pressure and viscous residue is obtained. The residue becomes solid upon addition of ether (50 ml). The solid is triturated, collected by filtration, washed with ether and dried over phosphorus pentoxide. The procedure provides 7β-amino-3-[2-(N-carboethoxysulfamoyl)benzoyloxy]methyl-3-cephem-4-carboxylic acid (1.55 g).

IR(KBr): cm$^{-1}$ 3230, 1771, 1730

NMR($d_6$-DMSO): δ 1.11(3H, t, J=7 Hz, —CH$_2$C$\underline{H}_3$), 3.66(2H, broad, 2—CH$_2$), 4.00(2H, q, J=7 Hz, —C$\underline{H}_2$CH$_3$), 4.94(2H, ABq, J=14 Hz, 3—CH$_2$), 5.02(1H, d, J=5 Hz, 6—H), 5.26(1H, d, J=5 Hz, 7—H), 7.55–8.13(4H, m, arom-H)

EXAMPLE 22

In water (2 ml) containing sodium salt of 5-mercapto-1H-1,2,3-triazole (120 mg) and sodium hydroxide (40 mg) is dissolved under ice cooling 7β-amino-3-[2-(N-carboethoxycarbamoyl)benzoyloxy]methyl-3-cephem-4-carboxylic acid (450 mg) and to the mixture is added diluted hydrochloric acid to adjust its pH to 5.5 under stirring, followed by further stirring for one hour at 60° C. To the solution, is added methanol (5 ml) and the mixture is allowed to cool to the room temperature. The cooled mixture is adjusted its pH to 3.9 by adding diluted hydrochloric acid under stirring and the resultant mixture is further stirred for one hour under ice-cooling. The precipitate is collected by filtration and washed with water and methanol in this order and then dried over phosphorus pentoxide. The procedure provides 7β-amino-3-(1H-1,2,3-triazol-5-yl)thiomethyl-3-cephem-4-carboxylic acid (193 mg).

IR(KBr): cm$^{-1}$ 1800, 1525

EXAMPLE 23

While a solution of diketene (0.01 ml) in dichloromethane (1 ml) is stirred at −50°–−40° C., 1.0 M bromine solution in dichloromethane (1.40 ml) is added dropwise for five minutes and stirred for 20 minutes. Separately, 7β-amino-3-[2-(N-carboethoxysulfamoyl)benzoyloxy]methyl-3-cephem-4-carboxylic acid (475 mg) is suspended in dichloromethane (3 ml) and cooled to −40° C., followed by the addition of triethylamine (0.42 ml) in dichloromethane (3 ml). This solution is added to the above reaction mixture at −40°–−30° C. After stirring for 10 minutes, the mixture is further stirred under cooling with ice for 30 minutes. Then, dichloromethane is distilled off under reduced pressure. To the residue, 10% phosphoric acid (5 ml), water (10 ml), tetrahydrofuran (2 ml) and ethyl acetate (10 ml) are added and the mixture is stirred vigorously. The organic layer is washed with a saturated solution of sodium chloride and dried. The solvent is distilled off and ether (20 ml) is added. The procedure provides 7β-(4-bromo-3-oxobutylamido)-3-[2-(N-carboethoxysulfamoyl)benzoyloxy]methyl-3-cephem-4-carboxylic acid (0.5 g).

NMR($d_6$-DMSO): δ 1.1(3H, t, —CH$_2$C$\underline{H}_3$), 3.63(4H, broad, —CH$_2$CO, 2—CH$_2$), 4.02(2H, q, —C$\underline{H}_2$CH$_3$), 4.39(2H, s, BrCH$_2$—), 5.05 (1H, d, J=5 Hz, 6—H), 5.17(2H, ABq, J=13 Hz, 3—CH$_2$), 5.70 (1H, dd, J=5 & 8Hz, 7—H), 7.6–8.1(4H, m,

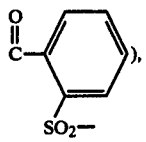

9.06(1H, d, J=8Hz, —CONH—)

EXAMPLE 24

7β-(Thienylacetamido)-3-[2-(N-carboethoxysulfamoyl)benzoyloxy]methyl-3-cephem-4-carboxylic acid-etherate (619 mg), sodium azide (100 mg) and sodium bicarbonate (84 mg) are dissolved in phosphate buffer solution (pH 6.4) (10 ml) and the mixture is stirred at 60° C. for one hour. After cooling, the reaction mixture is acidified by phosphoric acid and extracted with ethyl acetate. The ethyl acetate layer is dried and concentrated under reduced pressure. The residue is triturated with ether. The procedure provides 7β-(thienylacetamido)-3-azidomethyl-3-cephem-4-carboxylic acid.

IR(KBr): cm$^{-1}$ 2110

EXAMPLE 25

7β-Phenylacetamido-3-hydroxymethyl-3-cephem-4-carboxylic acid triethylamine salt (450 mg) is dissolved in dichloromethane (5 ml), followed by the addition of N-carboethoxy-4-nitrophthalimide (330 mg) and triethylamine (0.14 ml). The mixture is stirred at room temperature overnight. The solvent is distilled off and to the residue, ethyl acetate (20 ml) and water (20 ml) are added. After separation, aqueous layer is washed with ethyl acetate and acidified to pH 2.0 and extracted with ethyl acetate. The ethyl acetate layer is dried and concentrated. Ether is added to the residue and the resultant powder is collected by filtration. The procedure provides 7β-phenylacetamido-3-[2-(N-ethoxycarbamoyl)-4(or 5)-nitrobenzoyloxy]methyl-3-cephem-4-carboxylic acid (420 mg).

IR(KBr): cm$^{-1}$ 1776, 1735

NMR(d$_6$-DMSO): δ 1.17(3H, t, CH$_2$CH$_3$), 3.57(2H, s, —CH$_2$CO—), 3.65(2H, board, 2—CH$_2$), 4.06(2H, q, —CH$_2$CH$_3$), 5.01 & 5.35(2H, ABq, J=13 Hz, 3—CH$_2$), 5.13(1H, d, J=5 Hz, 6—H), 5.73(1H, dd, J=5 & 8Hz, 7—H)

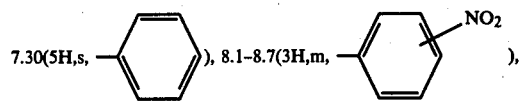

9.09(1H, d, —CONH—)

EXAMPLE 26

In acetonitrile (10 ml) is dissolved 7β-{D-5-(p-toluenesulfonamido)-5-carboxyvaleramido}-3-hydroxymethyl-3-cephem-4-carboxylic acid ditriethylamine salt (729 mg), followed by the addition of triethylamine (202 mg), 5-mercapto-1-methyl-1H-tetrazole (232 mg) and N-carboethoxyisatin (438 mg) in the order mentioned. The solution is reacted at room temperature for 3 hours and then, the solvent is distilled off under reduced pressure. The residue is dissolved in water-ethyl acetate, adjusted to pH 2.0 and extracted with ethyl acetate. The organic layer is washed with water and, following the addition of water, is adjusted to pH 5.0 with sodium hydrogen carbonate. Aqueous solution is concentrated and the residue is subjected to column chromatography on Amberlite XAD-2. Elution is carried out with a mixture of water-methanol and the eluate is collected and concentrated. The concentrate is acidified and extracted with ethyl acetate. The extract is dried and concentrated.

The procedure provides 7β-{D-5-(p-toluenesulfonamido)-5-carboxyvaleramido}-3-(1-methyl-1H-tetrazol-5-yl)thiomethyl-3-cephem-4-carboxylic acid.

IR(KBr): cm$^{-1}$ 3275, 1780, 1727, 1635, 1535

NMR(d$_6$-DMSO): δ 1.45–1.78(4H, m), 2.0–2.3(2H, m), 2.41(3H, s, —CH$_3$), 3.71(2H, broad, 2—CH$_2$), 3.95(3H, s, —NCH$_3$), 4.28(2H, broad), 5.06(1H, d, J=5 Hz, 6—H), 5.62(1H, dd, J=5.0 & 9.0 Hz, 7—H)

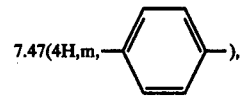

7.91(1H, d, J=9.0 Hz), 8.68(1H, d, J=9.0Hz)

EXAMPLE 27

In a mixture of water (50 ml) and tetrahydrofuran (30 ml) is dissolved 7β-(D-5-phthalimido-5-carboxyvaleramido)-3-[2-(N-carboethoxycarbamoyl)benzoyloxy]methyl-3-cephem-4-carboxylic acid (7.23 g) together with 2-carbamoylmethylthio-5-mercapto-1,3,4-thiadiazole (2.28 g) and sodium bicarbonate (2.20 g). The solution is adjusted to pH 5.8 and reacted at 60° C. for one hour. After cooling, the solution is adjusted to pH 5.0, washed twice with ethyl acetate and brought down to pH 2.0 with diluted hydrochloric acid. Then, it is extracted three times with a solvent mixture of ethyl acetate and tetrahydrofuran (2:1) and the organic layer is washed with a saturated aqueous solution of sodium chloride and dried over magnesium sulfate. The solvent is distilled off and the residue is treated with ethyl acetate. The resultant powder is collected by filtration, washed with ethyl acetate and dried. The procedure provides 7β-(D-5-phthalimido-5-carboxyvaleramido)-3-(2-carbamoylmethylthio-1,3,4-thiadiazol-5-yl)thiomethyl-3-cephem-4-carboxylic acid (5.70 g).

IR(KBr): cm$^{-1}$ 3430, 3340, 1776, 1717, 1680, 1535

NMR(d$_6$-DMSO): δ 1.30–2.40(6H, m), 3.57(2H, br), 4.40(2H, s), 4.32(2H, ABq, J=12Hz), 4.70(1H, t, JL32 8 Hz), 5.0(1H, d, J=5 Hz), 5.55(1H, dd, J=5 & 8Hz), 7.20(1H, broad), 7.60 (1H, broad), 7.86(4H, s), 8.74(1H, d, J=8Hz)

EXAMPLE 28

In water (100 ml) is dissolved 7β-(D-5-phthalimido-5-carboxyvaleramido)-3-[2-(N-carboethoxycarbamoyl)-benzoyloxy]methyl-3-cephem-4-carboxylic acid (3.62 g) together with 2-(2-hydroxyethylthio)-5-mercapto-1,3,4-thiadiazole (1.45 g) and sodium bicarbonate (1.1 g). The solution is adjusted to pH 5.5 and reacted at 60° C. for 50 minutes. The aqueous solution is washed twice with ethyl acetate, brought down to pH 2.0 with diluted hydrochloric acid and extracted three times with a mixture of ethyl acetate and tetrahydrofuran (4:1). The organic layer is washed with a saturated aqueous solution of sodium chloride, dried over magnesium sulfate, filtered and distilled off the solvent. The procedure provides 7β-(D-5-phthalimido-5-carboxyvaleramido)-3-[2-(2-hydroxyethylthio)-1,3,4-thiadiazol-5-yl]-thiomethyl-3-cephem-4-carboxylic acid (3.15 g).

IR(KBr): cm$^{-1}$ 3325, 1780, 1715, 1645, 1530

NMR(d$_6$-DMSO): δ 1.30–2.40(6H, m), 3.20–3.80(6H, m), 4.27(2H, ABq, J=12 Hz), 4.65(1H, t, J=9 Hz), 4.96(1H, d, J=5 Hz), 5.55(1H, dd, J=5 & 8Hz), 7.87(4H, s), 8.70(1H, d, J=8 Hz)

EXAMPLE 29

7β-(2-Thienylacetamido)-3-[2-(N-carboethoxysulfamoyl)-benzoyloxy]methyl-3-cephem-4-carboxylic acid (619 mg) is dissolved in water (5 ml) together with sodium hydrogen carbonate (170 mg), potassium iodide (400 mg) and pyridine (210 mg). The solution is adjusted to pH 6.5 and then stirred at 60° C. for one hour and a half. After cooling, the reaction mixture is subjected to column chromatography on Amberlite XAD-2. Elution is carried out with water and then, with a mixture of water-methanol. The fractions containing the desired product are pooled, concentrated and lyophilized. The procedure provides 7β-(2-thienylacetamido)-3-(pyridiniummethyl)-3-cephem-4-carboxylate (220 mg).

IR(KBr): cm$^{-1}$ 1763, 1698, 1617

NMR(D$_2$O): δ 3.17 & 3.67(2H, ABq, J=17 Hz, 2—CH$_2$), 3.38(2H, s, —CH$_2$CO—), 5.19(1H, d, J=5 Hz, 6—H), 5.41 & 5.67(2H, ABq, J=14 Hz, 3—CH$_2$), 5.75(1H, d, J=5 Hz, 7—H), 7.01 & 7.28 3H, 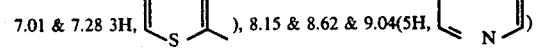 ), 8.15 & 8.62 & 9.04(5H,

EXAMPLE 30

7β-Amino-3-[2-(N-carboethoxycarbamoyl)benzoyloxy]-methyl-3-cephem-4-carboxylic acid (450 mg) is suspended in N,N-dimethylformamide (5 ml), followed by addition of O-carboxymandelic anhydride (267 mg). The mixture is stirred for 2 hours and poured into the mixed solution of water (20 ml) and ethyl acetate (20 ml). After separation, the ethyl acetate layer is washed with water and then extracted with aqueous sodium bicarbonate solution. The aqueous layer is purified by column chromatography on Sephadex LH-20. The main fraction is collected and lyophilized. The procedure provides sodium 7β-mandelamido-3-[2-(N-carboethoxycarbamoyl)benzoyloxy]methyl-3-cephem-4-carboxylate (180 mg).

IR(KBr): cm$^{-1}$ 1770, 1505

NMR(d$_6$-DMSO): δ 1.17(3H, t, —CH$_2$C$\underline{H}_3$), 3.47(2H, 2—CH$_2$), 4.08 (2H, q,—C$\underline{H}_2$CH$_3$), 4.9–5.4(4H, m), 5.59(1H, dd, 7–H), 7.2–8.0(9H, m)

EXAMPLE 31

7β-Amino-3-[2-(N-carboethoxysulfamoyl)benzoyloxy]-methyl-3-cephem-4-carboxylic acid (970 mg) is suspended in dichloromethane (20 ml), followed by the addition of triethylamine (0.84 ml) and D(—)-α-sulfophenylacetyl chloride (560 mg) under ice-cooling. The mixture is stirred for 30 minutes and after the addition of more triethylamine (0.2 ml), stirred further for 30 minutes. The solvent is distilled off to dryness and the residue is triturated with ether (60 ml). Thus obtained powder is collected by filtration, washed with ether and dried over phosphorus pentoxide. The powder is dissolved in water (8 ml) and under ice-cooling 1N-hydrochloric acid is added to adjust its pH to 1.0 and then a saturated aqueous solution of sodium chloride (12 ml) is added. The resultant precipitate is triturated, collected by filtration, washed with a saturated aqueous solution of sodium chloride and dried. Thus obtained powder is dissolved in tetrahydrofuran (40 ml) and the insolubles are filtered off. The filtrate is concentrated to yield slurry. The slurry is triturated with ether (40 ml) and the resultant precipitate is collected by filtration and dried over phosphorus pentoxide. The procedure provides 7β-D-α-sulfophenylacetamido-3-[2-(N-carboethoxy-sulfamoyl)benzoyloxy]methyl-3-cephem-4-carboxylic acid (822 mg).

IR(KBr): cm$^{-1}$ 1780(sh), 1745, 1680

NMR(d$_6$-DMSO): δ 1.11(3H, t, J=8 Hz —CH$_3$), 3.60(2H, broad, 2—CH$_2$), 4.03(2H, q, J=8 Hz, —C$\underline{H}_2$CH$_3$), 5.07(1H, s,

5.09 (1H, d, J=4.5 Hz, 6—H), 5.18(2H, ABq, J=13Hz, 3—CHJ$_2$), 5.78 (1H, q, J=4.5 & 8Hz &—H), 7.6–8.15(9H, m, arom-H)

EXAMPLE 32

In acetone (1 ml) is dissolved 7β-(4-bromo-3-oxobutylamido)-3-[2-(N-carboethoxysulfamoyl)benzoyloxy]methyl-3-cephem-4-carboxylic acid (319 mg) and, under ice-cooling, water (1 ml) and thiourea (42 mg) is added. Then, sodium hydrogen carbonate (42 mg) and water (1 ml) are added. The mixture is reacted at room temperature for 5 hours, after which time it is cooled with ice. The resultant crystals are collected by filtration, washed with water and ether and dried. The procedure provides 7β-(2-imino-4-thiazolin-4-yl)acetamido-3-[2-(N-carboethoxysulfamoyl)benzoyloxy]methyl-3-cephem-4-carboxylic acid.

NMR(d$_6$-DMSO): δ 1.10(3H, t, CH$_2$C$\underline{H}_3$), 3.38(2H, s, —CH$_2$CONH), 3.58(2H, broad, 2—CH$_2$), 4.01(2H, q, C$\underline{H}_2$CH$_3$), 5.07(1H, d, J=5 Hz, 6—H), 5.17(2H, ABq, J=13 Hz, 3—CH$_2$), 5.70(1H, dd, J=5 & 8Hz, 7—H), 6.23(1H, s, thiazolin-H)

EXAMPLE 33

In 50% aqueous acetone (12 ml), is dissolved 7β-(D-5-phthalimido-5-carboxyvaleramido)-3-[2-(N-carboethoxycarbamoyl)benzoyloxy]methyl-3-cephem-4-carboxylic acid (723 mg), followed by the addition of indole (0.35 g) and sodium hydrogen carbonate (0.17 g). The mixture is stirred at 60° C. for one hour. After cooling, most of the acetone is distilled off under reduced pressure. Then 5% aqueous phosphoric acid solution (15 ml) and ethyl acetate (30 ml) are added. The ethyl acetate layer is washed with a saturated aqueous solution of sodium chloride, dried and concentrated. To the residue, ether is added and the resultant powder is collected by filtration. This powder is suspended in water and dissolved by the addition of sodium hydrogen carbonate (0.17 g). The solution is subjected to column chromatography on Sephadex LH-20, elution being carried out with water. The fractions containing the desired product are pooled and lyophilized. The procedure provides 7β-(D-5-phthalimido-5- carboxyvaleramido)-3-(3-indolyl)methyl-3-cephem-4-carboxylic acid disodium salt (0.24 g).

IR(KBr): cm$^{-1}$ 1758, 1702, 1600

NMR(D$_2$O): δ 1.68 & 2.26(6H, —(CH$_2$)$_3$—), 2.45 & 2.82(2H, ABq, J=18 Hz, 2—CH$_2$), 3.61 & 3.86(2H, ABq, J=15 Hz, 3—CH$_2$), 4.6–4.9(2H, —CH— & 6—H), 5.46(1H, d, J=5 Hz, 7—H), 7.0–7.8 (10H,

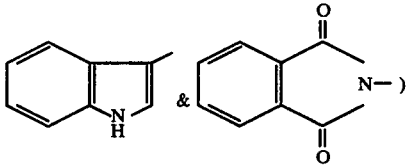

EXAMPLE 34

In 50% aqueous acetone (8 ml) is dissolved 7β-thienylacetamido-3-[2-(N-carboethoxysulfamoyl)benzoyloxy]methyl-3-cephem-4-carboxylic acid-etherate (619 mg), together with acetylacetone (0.5 g) and sodium hydrogen carbonate (0.17 g). The mixture is stirred at 60° C. for one hour. After cooling, most of the acetone is distilled off under reduced pressure. To the residue, ethyl acetate (20 ml) and diluted phosphoric acid are added. The ethyl acetate layer is washed with a saturated aqueous solution of sodium chloride, dried over magnesium sulfate and concentrated. To the residue, ether is added and the resultant powder is collected by filtration. This powder is suspended in water and dissolved by the addition of sodium hydrogen carbonate. The solution is subjected to column chromatography on Sephadex LH-20, elution being carried out with water. The desired fractions are pooled and lyophilized. This product is dissolved in water and acidified with diluted phosphoric acid and extracted with ethyl acetate (20 ml). The ethyl acetate layer is washed with water, dried over magnesium sulfate and concentrated under reduced pressure. To the residue, ether is added and triturated. The resultant powder is collected by filtration, washed with ether and dried. The procedure provides 7β-thienylacetamido-3-(2-acetyl-3-oxo)butyl-3-cephem-4-carboxylic acid.

IR(KBr): cm$^{-1}$ 1765, 1718

NMR(d$_6$-DMSO): δ 2.13 & 2.18(6H, s, (COCH$_3$)$_2$), 2.6–3.1(2H, m, 3—CH$_2$), 3.31 & 3.56(2H, ABq, 2—CH$_2$), 3.75(2H, s, —CH$_2$CO—), 4.14(1H, —CH—), 5.01(1H, d, J=5 Hz, 6—H), 5.58(1H, dd, J=5 & 8 Hz, 7—H), 6.92 & 7.30(3H, ), 9.04(1H, d, J=8 Hz, —CONH—)

EXAMPLE 35

(1) Sodium 7β-(t-butoxycarbonyl)amino-3-hydroxymethyl-3-cephem-4-carboxylate (1.60 g) is dissolved in N,N-dimethylformamide (8 ml), followed by addition of triethylamine (2 ml) and N-carboethoxyphthalimide (1.65 g) under stirring and ice-cooling. After stirring for one hour at room temperature, the solution is poured into toluene (300 ml) and n-hexane (200 ml) is added. The resultant precipitate is collected by filtration, washed with toluene and dried. The powder thus obtained is dissolved in water (50 ml) under ice-cooling and ethyl acetate (50 ml) is added. Diluted phosphoric acid is added to adjust its pH to 4.0. After separation, the ethyl acetate layer is washed with water and water (10 ml) is added. To the mixture, sodium hydrogen carbonate is added to adjust its pH to 6.8.

The aqueous layer is washed with ethyl acetate and ethyl acetate (50 ml) is added. The mixture is treated at pH 4.0 in a similar way just mentioned above.

After separation, the ethyl acetate layer is washed with water, dried over anhydrous sodium sulfate and concentrated. To the residue, ether (70 ml) is added under stirring and the resultant insolubles are filtered off. The filtrate is concentrated (to 3 ml) under reduced pressure and carbon tetrachloride (50 ml) is added. The resultant precipitate is collected by filtration, washed with carbon tetrachloride and dried over phosphorus pentoxide. The procedure provides 7β-(t-butoxycarbonyl)-amino-3-[2-(N-carboethoxycarbamoyl)benzoyloxy]methyl-3-cephem-4-carboxylic acid (1.04 g).

IR(KBr): cm$^{-1}$ 1775, 1716

NMR(d$_6$-DMSO): δ 1.18(3H, t, J=8 Hz, —CH$_2$CH$_3$), 1.44(9H, s, C(CH$_3$)$_3$), 3.61(2H, ABq, J=18 Hz, 2—CH$_2$), 4.07(2H, q, J=8Hz, —CH$_2$CH$_3$ 5.08(1H, d, J=4.5, 6—H), 5.10(2H, ABq, J=13Hz, 3—CH$_2$), 5.44(1H, q, J=4.5 & 8Hz, 7—H), 7.30–7.96(4H, m, arom-H)

(2) 7β-(t-Butoxycarbonyl)amino-3-[2-(N-carboethoxycarbamoyl)benzoyloxy]methyl-3-cephem-4-carboxylic acid (275 mg) is dissolved in trifluoroacetic acid (2 ml) under ice-cooling and the mixture is stirred for 20 minutes. The solution is concentrated and to the residue, ether (20 ml) is added. The resultant precipitate is triturated, collected by filtration, washed with ether and dried over phosphorus pentoxide. The procedure provides 7β-amino-3-[2-(N-carboethoxycarbamoyl)-benzoyloxy]methyl-3-cephem-4-carboxylic acid (195 mg). In NMR spectrum, this product is good agreement with the product obtained in Example 20.

EXAMPLE 36

(1) In N,N-dimethylformamide (8 ml), is dissolved sodium 7β-(t-butoxycarbonyl)amino-3-hydroxymethyl-3-cephem-4-carboxylate (1.60 g), followed by addition of triethylamine (3 ml) and N-tosylphthalimide (1.80 g) under ice-cooling. The mixture is stirred for one hour and then poured into toluene (300 ml). n-Hexane (200 ml) is added and the resultant precipitate is collected by filtration, washed with toluene and dried. The powder thus obtained is dissolved in water (50 ml). The solution is adjusted to pH 3.7 with acetic acid and a saturated aqueous solution of sodium chloride (50 ml) is added. The resultant precipitate is collected by filtration and washed with water. The cake thus obtained is added to a mixed solution of ethyl acetate (30 ml) and water (10 ml). After separation, the ethyl acetate layer is washed with water and water (10 ml) is added. Sodium hydrogen carbonate is added to adjust to pH 6.8. After separation, the aqueous layer is washed with ethyl acetate and ethyl acetate (20 ml) is added. To the mixture, diluted phosphoric acid is added to adjust to pH 4.0. After separation, the ethyl acetate layer is washed with water, dried over anhydrous sodium sulfate and concentrated. To the residue, ether is added under stirring and the resultant insolubles are filtered off. The filtrate is concentrated under reduced pressure and carbon tetrachloride is added. The resultant precipitate is collected by filtration and dried over phosphorous pentoxide. The procedure provides 7β-(t-butoxycarbonyl)amino-3-[2-(N-tosylcarbamoyl)benzoyloxy]methyl-3-cephem-4-carboxylic acid (1.21 g).

IR(KBr): cm$^{-1}$ 1788, 1715

NMR(d$_6$-DMSO): δ1.44(9H, s, —C(CH$_3$)$_3$), 2.42(3H, s, —CH$_3$), 3.48 (2H, ABq, J=18 Hz, 2—CH$_2$), 4.93(2H, ABq, J=13 Hz, 3—CH$_2$), 5.04(1H, d, J=5 Hz, 6—H), 5.48(1H, q, J=5 & 8 Hz, 7—H), 7.40–7.93(8H, m, arom-H)

(2) 7β-(t-Butoxycarbonyl)amino-3-[2-(N-tosylcarbamoyl)benzoyloxy]methyl-3-cephem-4-carboxylic acid (631 mg) is dissolved in trifluoroacetic acid (2 ml) under ice-cooling. The solution is stirred for 20 minutes and concentrated under reduced pressure. To the residue, ether (20 ml) is added and the resultant solid is triturated. The powder thus obtained is collected by filtration, washed with ether and dried over phosphorus pentoxide. The procedure provides 7β-amino-3-[2-(N-tosylcarbamoyl)benzoyloxy]methyl-3-cephem-4-carboxylic acid (480 mg).

IR(KBr): cm$^{-1}$ 1782, 1715, 1680

NMR(D$_2$O+NaHCO$_3$): δ2.54(3H, s, —CH$_3$), 3.81(2H, ABq, J=18 Hz, 2—CH$_2$), 4.56(2H, ABq, J=12 Hz, 3—CH$_2$), 4.86(1H, d, J=5 Hz, 6—H), 5.16(1H, d, J=5 Hz, 7—H), 7.41–8.02(8H, m, arom-H)

EXAMPLE 37

7β-Amino-3-[2-(N-carboethoxysulfamoyl)benzoyloxy]methyl-3-cephem-4-carboxylic acid (457 mg) is suspended in a mixed solution of dichloromethane (5 ml) and N,N-dimethylformamide (1.0 ml) and to the mixture, a solution of (1H-tetrazol-1-yl)acetyl chloride (161 mg) in tetrahydrofuran (2 ml) is added over a period of 20 minutes and stirred for 2 hours. The solvent is distilled off under reduced pressure and to the resultant viscous residue, ethyl acetate (50 ml) and water (20 ml) are added and stirred. After separation, the ethyl acetate layer is washed with water, dried over anhydrous sodium sulfate and concentrated. To the concentrate (5 ml), chloroform (50 ml) is added and the resultant precipitate is filtered off. The filtrate is concentrated and to the concentrate (5 ml), ether (50 ml) is added. The resultant precipitate is collected by filtration and dried over phosphorous pentoxide. The procedure provides 7β-(1H-tetrazol-1-yl)acetamido-3-[2-(N-carboethoxysulfamoyl)benzoyloxy]methyl-3-cephem-4-carboxylic acid (216 mg).

IR(KBr): cm$^{-1}$ 1782, 1745

NMR(d$_6$-DMSO): δ1.13(3H, t, J=7 Hz, —CH$_2$C$\underline{H}_3$), 3.70(2H, broad, 2—CH$_2$), 4.05(2H, q, J=7 Hz, —C$\underline{H}_2$CH$_3$), 5.15(1H, d, J=4.5 Hz, 6—H), 5.22(2H, ABq, J=13.5 Hz, 3—CH$_2$), 5.40(2H, s, —N—CH$_2$), 5.78(1H, q, J=4.5 & 8 Hz, 7—H), 7.64–8.14(4H, m, arom-H), 9.35(1H, s, tetrazole-H), 9.49(1H, d, J=8 Hz, 7—CONH—)

EXAMPLE 38

In water (5 ml) are dissolved 7β-(2-imino-4-thiazolin-4-yl)acetamido-3-[2-(N-carboethoxysulfamoyl)benzoyloxy]methyl-3-cephem-4-carboxylic acid (313 mg), 5-mercapto-1-[2-(N,N-dimethylamino)ethyl]-1H-tetrazole (113 mg) and sodium hydrogen carbonate (42 mg) and the resultant solution is heated at 55° C. for 60 minutes. The reaction solution is adjusted its pH to 5.8 and purified by column chromatography on Amberlite XAD-2 and the fractions rich in the desired product are pooled and lyophilized. The procedure provides 7β-(2-imino-4-thiazolin-4-yl)acetamido-3-{1-[2-(N,N-dimethylamino)ethyl]-1H-tetrazol-5-yl}thiomethyl-3-cephem-4-carboxylic acid.

IR(KBr): cm$^{-1}$ 1765

NMR(D$_2$O): δ3.06(6H, s, —N(CH$_3$)$_2$), 3.5–4.8(10H, m), 5.12(1H, d, J=5 Hz, 6—H), 5.65(1H, d, J=5 Hz, 7—H), 6.62(1H, s, thiazolin-H)

EXAMPLE 39

7β-(D-α-Sulfophenylacetamido)-3-[2-(N-carboethoxysulfamoyl)benzoyloxy]methyl-3-cephem-4-carboxylic acid (341 mg) is dissolved in water (0.3 ml) by the addition of sodium hydrogen carbonate (84 mg) and then isonicotinamide (90 mg) and KSCN (1.2 g) are added. The mixture is heated at 60° C. for one hour and then subjected to column chromatography on Amberlite XAD-2, elution being carried out with water. The fractions rich in the desired product are pooled, lyophilized and recrystallized from ethanol-water. The procedure provides 7β-(D-α-sulfophenylacetamido)-3-(4-carbamoylpyridinium)methyl-3-cephem-4-carboxylate sodium salt.

IR(KBr): cm$^{-1}$ 1765, 1692, 1645, 1615, 1029

NMR(D$_2$O): δ2.99 & 3.56(2H, ABq, J=18 Hz, 2—CH$_2$), 5.40 & 5.51 (2H, 3—CH$_2$), 5.13(1H, d, J=4.8, 6—H), 5.73(1H, d, J=4.8 Hz, 7—H),

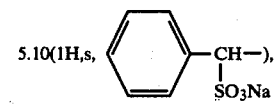

7.40(5H, m), 8.31 & 9.07(4H)

EXAMPLE 40

In a phosphate buffer solution of pH 6.4 (3 ml) are dissolved 5-mercapto-2-methyl-1,3,4-thiadiazole (79 mg), sodium hydrogen carbonate (92 mg) and 7β-(1H-tetrazol-1-yl)acetamido-3-[2-(N-carboethoxysulfamoyl)benzoyloxy]methyl-3-cephem-4-carboxylic acid (298 mg) and the resultant solution is heated at 60° C. for one hour. Then, the mixture is concentrated and the residue is subjected to column chromatography on Sephadex LH-20, elution being carried out with water. The fractions containing the desired product are pooled and lyophilized. The procedure provides sodium 7β-(1H-tetrazol-1-yl)acetamido-3-(2-methyl-1,3,4-thiadiazol-5-yl)thiomethyl-3-cephem-4-carboxylate. This product is in good agreement with the authentic sample in NMR spectrum.

What is claimed is:

1. A compound of the formula

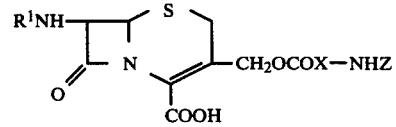

wherein R$^1$ is an acyl group, and X is a group having a carbonyl or sulfonyl at one terminal end thereof, said X being able to form with

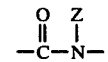

a five- or six-membered ring of the formula

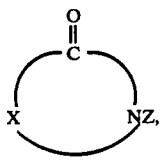

said five- or six-membered ring being N-carboethoxyphthalimide, N-carbomethoxyphthalimide, 4-nitro-N-carboethoxyphthalimide, 3-nitro-N-carboethoxyphthalimide, N-carboethoxysuccinimide, N-carbomethoxysuccinimide, N-tosylphthalimide, N-methylsulfonylphthalimide, N-benzenesulfonylphthalimide, N-acetyl-phthalimide, N-chloroacetylphthalimide, N-acetylsuccinimide, N-carboethoxysaccharin, N-acetylsaccharin, N-benzoylsaccharin, N-carboethoxymaleimide, N-carboethoxyglutarimide, N-carboethoxy-(p-chlorophenyl)succinimide, N-carboethoxyisatin, N-carbomethoxyisatin, N-acetylisatin, N-(methylcarbamoyl)isatin, N-(phenylcarbamoyl)isatin, N-(β-methylsulfonylethoxycarbonyl)isatin, N-(diethylphosphoro)succinimide, N-(dimethylphosphoro)succinimide, N-(dimethylphosphino)succinimide or N-(diethylphosphino)phthalimide,
or a salt thereof.

2. A compound as claimed in claim 1, wherein the salt is a pharmaceutically acceptable salt.

3. A compound as claimed in claim 1, wherein the salt is an alkali metal salt or an organic amine salt.

4. A compound as claimed in claim 1, wherein $R^1$ represents an acyl group the formula

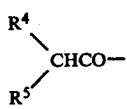

wherein $R^4$ represents acetyl, a halogenoacetyl, phenyl, p-hydroxyphenyl, thienyl, 2-imino-4-thiazolin-4-yl, 2-oxo-4-thiazolin-4-yl, tetrazolyl, phenoxy or 3-amino-3-carboxypropyl and $R^5$ represents hydrogen, sulfo, amino or hydroxy, and each of amino and carboxyl group in $R^4$ and $R^5$ may be protected.

5. A compound as claimed in claim 4, wherein the protective group for the amino group is phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, acetyl, valeryl, capryl, n-decanoyl, acryloyl, pivaloyl, camphorsulfonyl, methanesulfonyl, chloroacetyl, tert-butoxycarbonyl, ethoxycarbonyl, isobornyloxycarbonyl, phenyloxycarbonyl, trichloroethoxycarbonyl, benzyloxycarbonyl, β-methylsulfonylethoxycarbonyl, methylcarbamoyl, phenylcarbamoyl, naphthylcarbamoyl or 2-methoxycarbonyl-1-methylvinyl.

6. A compound as claimed in claim 1, wherein

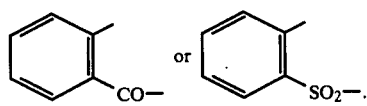

7. A compound according to claim 4, namely, 7β-(5-amino-5-carboxyvaleramido)-3-[2-(N-carboethoxycarbamoyl)benzoyloxy]methyl-3-cephem-4-carboxylic acid, wherein the amino group may be protected, or a salt thereof.

8. A compound according to claim 4, namely, 7β-(α-sulfophenylacetamido)-3-[2-(N-carboethoxysulfamoyl)-benzoyloxy]methyl-3-cephem-4-carboxylic acid or a salt thereof.

9. A compound according to claim 4, namely, 7β-(4-bromo-3-oxobutylamido)-3-[2-(N-carboethoxysulfamoyl)benzoyloxy]-methyl-3-cephem-4-carboxylic acid or a salt thereof.

10. A compound according to claim 4, namely 7β-(2-imino-4-thiazolin-4-yl)acetamido-3-[2-(N-carboethoxysulfamoyl)benzoyloxy]methyl-3-cephem-4-carboxylic acid or a salt thereof.

11. A compound according to claim 4, namely, 7β-(5-amino-5-carboxyvaleramido)-3-[2-(N-carboethoxysulfamoyl)benzoyloxy]methyl-3-cephem-4-carboxylic acid, wherein the amino group may be protected, or a salt thereof.

12. A compound according to claim 4, namely, 7β-(5-amino-5-carboxyvaleramido)-3-[2-(N-tosylcarbamoyl)-benzoyloxy]methyl-3-cephem-4-carboxylic acid, wherein the amino group may be protected, or a salt thereof.

13. A compound according to claim 4, namely, 7β-(5-amino-5-carboxyvaleramido)-3-[(2-ethoxycarbonylamino)phenylglyoxyloyloxy]methyl-3-cephem-4-carboxylic acid, wherein the amino group may be protected, or a salt thereof.

14. A compound according to claim 4, namely, 7β-(2-thienylacetamido)-3-[2-(N-carboethoxysulfamoyl)benzoyloxy]methyl-3-cephem-4-carboxylic acid or a salt thereof.

15. A compound according to claim 4, namely, 7β-phenylacetamido-3-[2-(N-carboethoxysulfamoyl)benzoyloxy]methyl-3-cephem-4-carboxylic acid or a salt thereof.

16. A compound according to claim 4, namely, 7β-(2-thienylacetamido)-3-[2-(N-tosylcarbamoyl)benzoyloxy]methyl-3-cephem-4-carboxylic acid or a salt thereof.

17. A compound according to claim 4, namely, 7β-(2-thienylacetamido)-3-[3-(N-carboethoxycarbamoyl)-propionyloxy]methyl-3-cephem-4-carboxylic acid or a salt thereof.

18. A compound according to claim 4, namely, 7β-phenylacetamido-3-[2-(N-ethoxycarbamoyl)-4(or 5)-nitrobenzoyloxy]methyl-3-cephem-4-carboxylic acid or a salt thereof.

19. A compound according to claim 4, namely, 7β-mandelamido-3-[2-(N-carboethoxycarbamoyl)benzoyloxy]methyl-3-cephem-4-carboxylic acid or a salt thereof.

20. A compound according to claim 4, namely, 7β-(1H-tetrazol-1-yl)acetamido-3-[2-(N-carboethoxysulfamoyl)benzoyloxy]methyl-3-cephem-4-carboxylic acid or a salt thereof.

21. A compound according to claim 4, namely, 7β-(D-5-phthalimido-5-carboxyvaleramido)-3-[2-(N-carboethoxycarbamoyl)benzoyloxy]methyl-3-cephem-4-carboxylic acid or a salt thereof.

22. A compound according to claim 4, namely, 7β-(D-5-phthalimido-5-carboxyvaleramido)-3-[2-(N-carboethoxysulfamoyl)benzoyloxy]methyl-3-cephem-4-carboxylic acid or a salt thereof.

23. A compound according to claim 4, namely, 7β-(D-5-benzamido-5-carboxylvaleramido)-3-[2-(N-tosylcarbamoyl)benzoyloxy]methyl-3-cephem-4-carboxylic acid or a salt thereof.

24. A compound according to claim 4, namely, 7β[(D-5-(p-t-butylbenzamido)-5-carboxyvaleramido]-3-[2-(N-carboethoxysulfamoyl)benzoyloxy]methyl-3-cephem-4-carboxylic acid or a salt thereof.

25. A compound of the formula

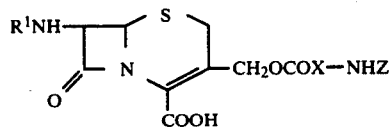

wherein R¹ is an acyl group, X is

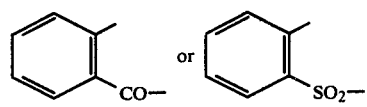

and Z is methoxycarbonyl, ethoxycarbonyl, acetyl, propionyl, benzoyl, chloroacetyl, phenylsulfonyl, tosyl, mesyl, carbamoyl, diethylphosphoro, dimethylphosphono, diethylphosphino or dimethylphosphino, or a salt thereof.

* * * * *